(12) United States Patent
Hudon et al.

(10) Patent No.: US 11,751,837 B2
(45) Date of Patent: Sep. 12, 2023

(54) X-RAY IMAGING APPARATUS AND X-RAY IMAGE PROCESSING METHOD

(71) Applicant: Shimadzu Corporation, Kyoto (JP)

(72) Inventors: Frederic Hudon, Laval (CA); Michel Archambault, Laval (CA)

(73) Assignee: Shimadzu Corporation, Kyoto (JP)

( * ) Notice: Subject to any disclaimer, the term of this patent is extended or adjusted under 35 U.S.C. 154(b) by 45 days.

(21) Appl. No.: 17/308,631

(22) Filed: May 5, 2021

(65) Prior Publication Data

US 2021/0353245 A1 Nov. 18, 2021

(30) Foreign Application Priority Data

May 15, 2020 (JP) ................. 2020-085596

(51) Int. Cl.
*A61B 6/00* (2006.01)
*A61B 90/00* (2016.01)
*G06T 7/246* (2017.01)

(52) U.S. Cl.
CPC ............. *A61B 6/547* (2013.01); *A61B 6/463* (2013.01); *A61B 6/5241* (2013.01); *A61B 90/39* (2016.02); *G06T 7/246* (2017.01); *G06T 2207/10016* (2013.01); *G06T 2207/20221* (2013.01)

(58) Field of Classification Search
CPC ........... G06T 7/0012; G06T 7/30; G06T 7/33; G06T 7/38; G06T 2207/20212; G06T 2207/20216; G06T 2207/20221; A61B 6/46–466; A61B 6/547; A61B 6/5241
See application file for complete search history.

(56) References Cited

U.S. PATENT DOCUMENTS

| | | | |
|---|---|---|---|
| 2017/0213343 A1* | 7/2017 | Vaillant | A61B 6/50 |
| 2018/0247437 A1* | 8/2018 | Hoornaert | G06T 7/38 |
| 2019/0015056 A1 | 1/2019 | Sato et al. | |

FOREIGN PATENT DOCUMENTS

| | | |
|---|---|---|
| JP | 2014-083230 A | 5/2014 |
| JP | 2018526144 A | 9/2018 |
| JP | 2020018702 A | 2/2020 |
| WO | 2017/115432 A1 | 7/2017 |

OTHER PUBLICATIONS

Notice of Reasons for Refusal dated Apr. 25, 2023, together with a machine translation for corresponding Japanese Patent Application No. 2020-085596.

* cited by examiner

*Primary Examiner* — Carolyn A Pehlke
(74) *Attorney, Agent, or Firm* — Muir Patent Law, PLLC

(57) ABSTRACT

This X-ray imaging apparatus is provided with an image controller for generating a composite image by superimposing a plurality of X-ray images. The image controller includes a detection processing unit configured to detect both a marker for indicating a position of a predetermined target object to be indwelled in a body of a subject and a device to be placed in the body of the subject separately from the predetermined target object, in the generated X-ray image. The image controller includes a composition processing unit configured to generate the composite image by superimposing the plurality of X-ray images based on the detected marker and the detected device.

10 Claims, 11 Drawing Sheets

Stenotic site

Stenotic site

X-RAY IMAGING APPARATUS AND X-RAY IMAGE PROCESSING METHOD

CROSS-REFERENCE TO RELATED APPLICATIONS

The related application number JP2020-85596, entitled "X-RAY IMAGING APPARATUS AND X-RAY IMAGE PROCESSING METHOD", filed on May 15, 2020, invented by Frederic Hudon, and Michel Archambault, upon which this patent application is based is hereby incorporated by reference.

BACKGROUND OF THE INVENTION

Field of the Invention

The present invention relates to an X-ray imaging apparatus and an X-ray image processing method.

Description of the Background Art

Conventionally, an X-ray fluoroscopic imaging apparatus for fluoroscopically or continuously imaging a region containing a device inserted into a body of a subject is known. Such an apparatus is disclosed in, for example, Japanese Unexamined Patent Application Publication No. 2014-83230.

The X-ray fluoroscopic imaging apparatus described in Japanese Unexamined Patent Application Publication No. 2014-83230 is used in a coronary intervention (PCI: percutaneous coronary intervention) treatment for performing stent indwelling. In a coronary intervention treatment, a stent is placed at a stenosis of a coronary artery. In particular, the blood vessel is held from the inside by indwelling the stent with the stent expanded in the blood vessel by a balloon. In this way, the coronary artery is expanded to keep the blood flow normal.

In a coronary intervention treatment, when inserting a stent and a balloon into a blood vessel, X-ray imaging is performed to visually recognize the position of the stent. In order to improve the visibility of the stent, the X-ray fluoroscopic imaging apparatus described in Japanese Unexamined Patent Application Publication No. 2014-83230 acquires a plurality of X-ray images of a region including the device (stent) inserted into a body of a subject and detects a marker provided in the vicinity of the stent. Then, an integrated image (composite image) is generated by aligning and superimposing the plurality of images in such a manner that the detected markers overlap with each other. Then, by detecting the stent portion from the generated integrated image, an enlarged image of the stent portion is displayed.

However, like the X-ray fluoroscopic imaging apparatus as described in Japanese Unexamined Patent Application Publication No. 2014-83230, a marker indicating the position of a predetermined target object to be indwelled, such as, e.g., a stent, in a body of a subject is provided, for example, near both ends (portions) of the predetermined target object. Then, by performing the alignment based on the position of the marker, the integrated image (composite image) is generated with the position of the predetermined target object, such as, e.g., a stent, aligned.

Therefore, in a case where the shape of the predetermined target object, such as, e.g., a stent, differs in each of the captured X-ray images, the predetermined target object in the composite image is displayed as blurred even if the alignment is performed based on the position of the marker.

Therefore, it is desired to improve the visibility of the predetermined target object in the integrated image (composite image) even in a case where the predetermined target object differs in the shape in a plurality of X-ray images.

SUMMARY OF THE INVENTION

The present invention has been made to solve the above-described problems. One object of the present invention is to provide an X-ray imaging apparatus and an X-ray image processing method capable of improving the visibility of a predetermined target object in a composite image generated by superimposing a plurality of X-ray images even when the predetermined target object differs in shape in a plurality of X-ray images.

In order to attain the above-described object, an X-ray imaging apparatus according to the first aspect of the present invention includes:

an X-ray tube configured to irradiate a subject with X-rays;

an X-ray detector configured to detect the X-rays transmitted through the subject; and an image controller configured to generate a composite image by superimposing a plurality of X-ray images generated based on a detection signal output from the X-ray detector, wherein the image controller includes:

a detection processing unit configured to detect both a marker for indicating a position of a predetermined target object to be indwelled in a body of the subject and a device to be placed in the body of the subject separately from the predetermined target object, in the generated X-ray image; and a composition processing unit configured to generate the composite image by superimposing the plurality of X-ray images based on the marker and the device both detected by the detection processing unit.

An X-ray image processing method according to a second aspect of the present invention includes the steps of:

generating an X-ray image by detecting X-rays that have transmitted through a subject;

detecting both a marker for indicating a position of a predetermined target object to be indwelled in a body of a subject and a device to be placed in the body of the subject separately from the predetermined target object, in the generated X-ray image; and generating a composite image by superimposing the plurality of X-ray images based on the detected marker and the detected device.

In the X-ray imaging apparatus according to the first aspect of the present invention and the X-ray image processing method according to the second aspect of the present invention, both the marker for indicating the position of a predetermined target object to be indwelled in a body of a subject and a device to be placed in the body of the subject separately from the predetermined target object are detected in the generated X-ray image. A composite image is generated by superimposing a plurality of X-ray images based on the detected marker and the detected device.

Thus, in the generated X-ray image, it is possible to acquire the position of the predetermined target object in the body of the subject by detecting the marker, Also, in the generated X-ray image, by detecting the device placed in the body of the subject, it is possible to detect the changes in the position and the shape of the device due to the movements in the body of the subject in each of the generated X-ray image. Therefore, in each of the generated X-ray images, the movements in the body of the subject can be acquired indirectly, so that the change in the shape of the predetermined target object indwelled in the body of the subject can be acquired indirectly.

Then, in the present invention, by detecting both the marker and the device, it is possible to acquire a change in the relative position and the relative shape of the predetermined target object with respect to the marker in the body of the subject. Therefore, when superimposing a plurality of X-ray images, the plurality of X-ray images can be superimposed in such a manner that the blur is reduced, based on the position and the shape of the predetermined target object reflected in each of the plurality of X-ray images. As a result, even in a case where the shape of the predetermined target object differs in each of the plurality of X-ray images, the visibility of the predetermined target object can be improved in the composite image generated by superimposing the plurality of X-ray images.

DESCRIPTION OF THE PREFERRED EMBODIMENT

Hereinafter, an embodiment in which the present invention is embodied will be described with reference to the attached figures.

(Overall Configuration of X-Ray Imaging Apparatus)

Referring to FIG. 1 to FIG. 13, an X-ray imaging apparatus 100 according to an embodiment of the present invention will be described.

Figure 1:
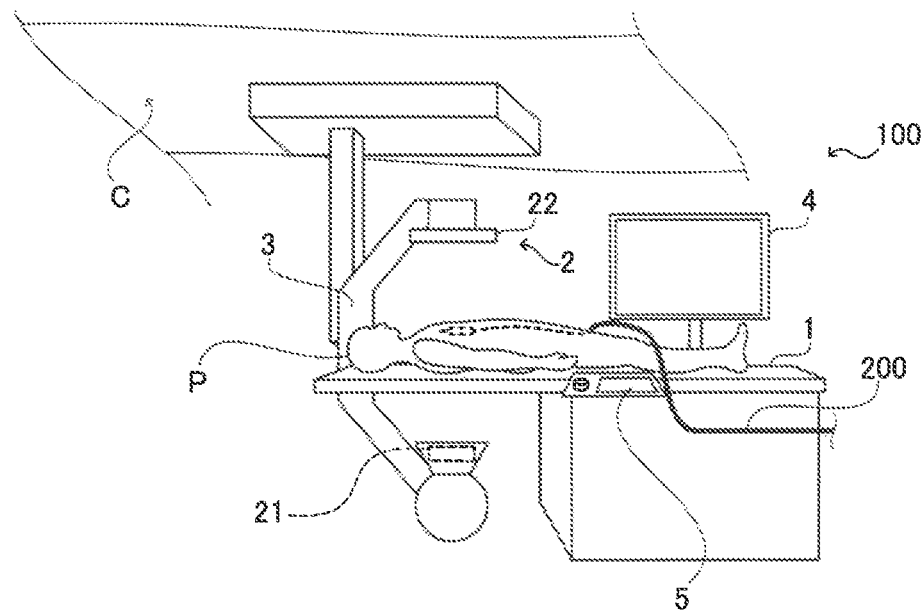
FIG. 1 is a diagram for explaining the configuration of an X-ray imaging apparatus according to one embodiment of the present invention.

As shown in FIG. 1, the X-ray imaging apparatus 100 according to this embodiment emits X-rays to a subject P into which a treatment device 200 has been inserted. The X-ray imaging apparatus 100 performs X-ray imaging by detecting the X-rays that have passed through the subject P. Then, the X-ray imaging apparatus 100 performs image processing on the X-ray image A (see FIG. 3) generated by performing X-ray imaging.

The X-ray imaging apparatus 100 generates an image for confirming, for example, the inside of a body of a subject P when performing a percutaneous coronary intervention (PCI: Percutaneous Coronary Intervention) treatment. The percutaneous coronary intervention treatment is a treatment that uses a treatment device 200 to resolve stenosis and occlusion of a blood vessel in a patient with angina pectoris or myocardial infarction caused by stenosis or occlusion of a coronary artery of a heart.

(Description of Treatment Device)

Figure 2A:
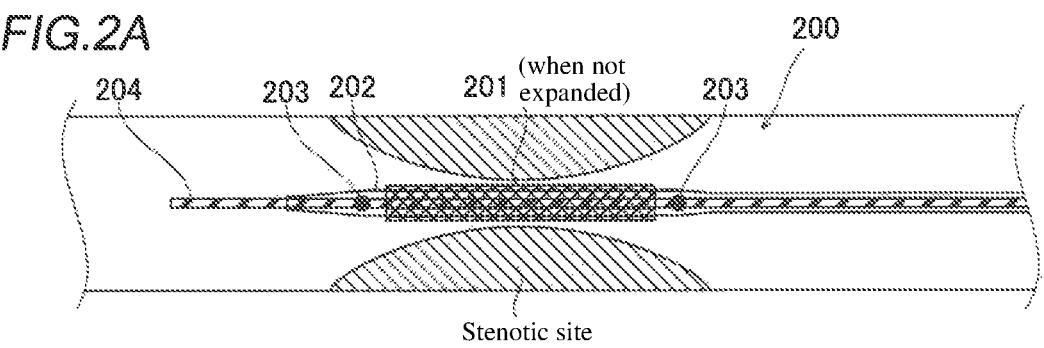
FIG. 2A is a diagram for explaining a treatment device according to an embodiment of the present invention and is a view showing a state before inflating a balloon.
Figure 2B:
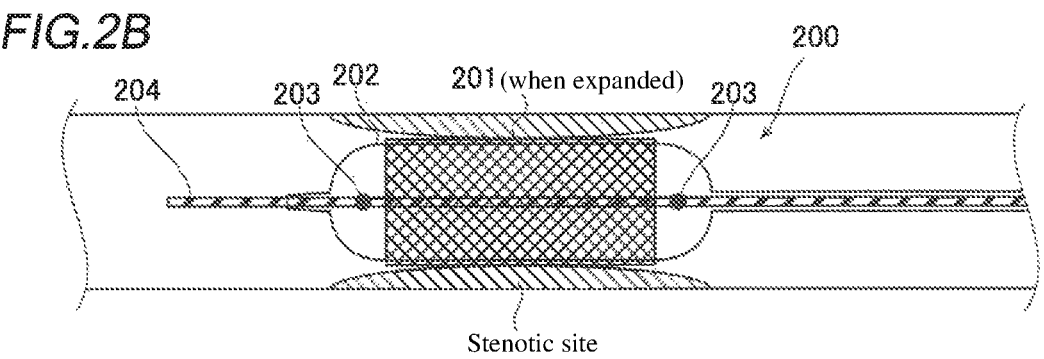
FIG. 2B is a view for explaining the treatment tool according to the embodiment and is a view showing a state after inflating the balloon.

In a percutaneous coronary intervention treatment, as shown in FIG. 2A and FIG. 2B, a treatment device 200 is used to treat stenosis of a coronary artery. The treatment tool 200 includes a stent 201, a balloon 202, a marker 203, and a guidewire 204. The stent 201 is an example of the "predetermined target object" recited in claims. The guidewire 204 is an example of the "device" recited in claims.

Figure 3:
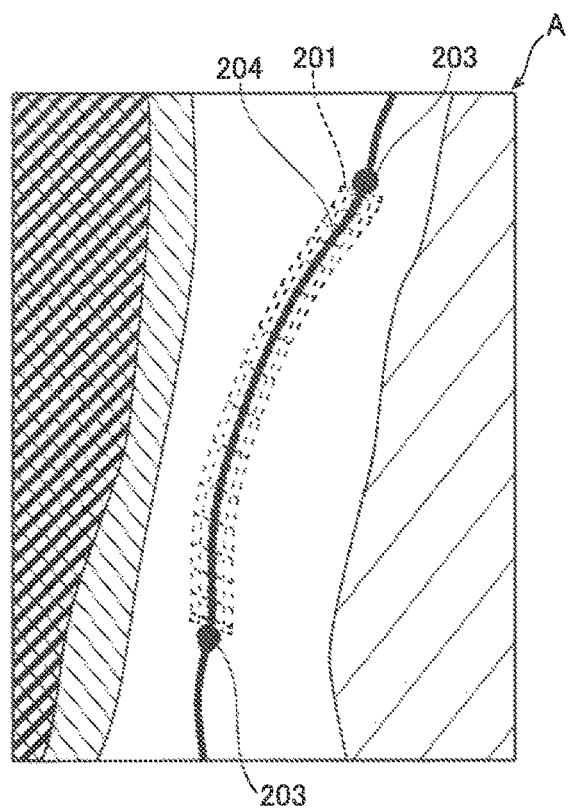
FIG. 3 is a diagram for illustrating an example of an X-ray image according to one embodiment.

The stent 201 has a thin mesh structure formed of metal such as stainless steel and is formed in a cylindrical shape. The stent 201 is indwelled in the body of the subject P by a percutaneous coronary intervention treatment. That is, the stent 201 is indwelled in the expanded stenotic site after performing a treatment for expanding the stenotic site of the coronary artery of the subject P (therapy for relieving the stenosis of the blood vessel). The stent 201 indwelled in the blood vessel retains the coronary artery (blood vessel) from the inside to prevent the reoccurrence of the stenosis (blockage) of the blood vessel. In addition, as shown in FIG. 3, the stent 201 readily transmits X-rays and is hard to be reflected in the X-ray image A. That is, in the X-ray image A, the visibility of the stent 201 is low.

The balloon 202 is a balloon provided at the distal end of a balloon catheter. A stent 201 is attached to the balloon 202. Then, as shown in FIG. 2B, the balloon 202 is configured to push and expand the stenotic site by bulging in the blood vessel of the subject P. In accordance with the inflation of the balloon 202, the stent 201 attached to the balloon 202 is expanded integrally with the balloon 202.

The marker 203 is provided at the balloon 202 (balloon catheter). The marker 203 is made of a material low in X-ray transparency (or an X-ray impermeable material). The marker 203 is high in visibility in the X-ray image A (see FIG. 3). The marker 203 is provided to confirm the position of the stent 201 when performing a percutaneous coronary intervention treatment. The marker 203 is provided at each of both ends of the stent 201, for example, to show the position of the stent 201 in the X-ray image A.

The guidewire 204 is used to place the stent 201 in the body of the subject P. Specifically, the guidewire 204 is used for causing the balloon 202 (balloon catheter) to which the stent 201 is attached to reach the stenotic site of the blood vessel (coronary artery) of the subject P. The stent 201 and the balloon 202 are caused to reach the position (stenotic site of coronary artery) where the balloon 202 is inflated using the guidewire 204 inserted from a blood vessel (such as the radial or femoral artery) of the wrist, thigh, etc.

Like the marker 203, the guidewire 204 is made of an (X-ray impermeable) material that is less transparent to X-rays. That is, the guidewire 204 is high in visibility in the X-ray image A (see FIG. 3). Further, the guidewire 204 is made of a flexible material so that it can be inserted into a blood vessel of a human body.

In other words, the guidewire 204 is inserted into a body of a subject P (into a blood vessel) while changing the shape according to the shape of the blood vessel of the subject P. Then, the guidewire 204 changes in shape integrally with the stent 201 in the body of the subject P. In other words, the stent 201 and the balloon 202 are configured to be allowed to reach the target position (the stenotic site in the blood vessel) in the blood vessel while deforming the shape integrally with the guidewire 204.

As described above, in a percutaneous coronary intervention treatment, the treatment device 200 is configured to perform a treatment on a blood vessel stenosis by positioning the balloon 202 with the stent 201 to the stenotic site using the guidewire 204 inserted into a blood vessel and inflating the balloon 202 integrally with the stent 201.

(Configuration of X-Ray Imaging Apparatus)

Figure 4:
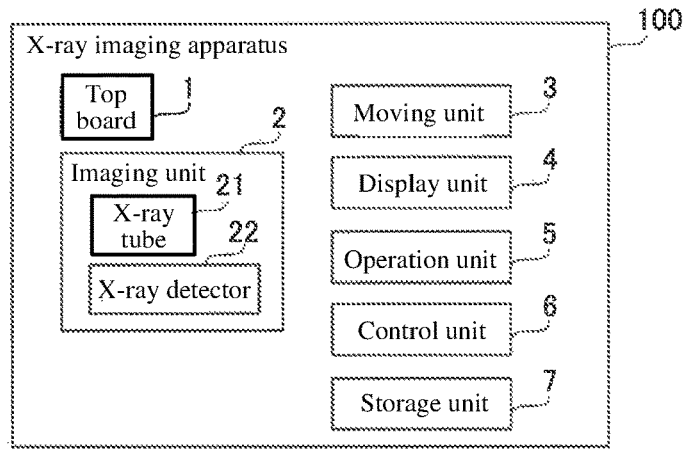
FIG. 4 is a block diagram for explaining the configuration of the X-ray imaging apparatus according to the embodiment.

The X-ray imaging apparatus 100 in this embodiment is provided with, as shown in FIG. 1 and FIG. 4, a top board 1, an imaging unit 2, a moving unit 3, a display unit 4, an operation unit 5, a control unit 6, and a storage unit 7. The control unit 6 is an example of the "image controller" recited in claims.

The top board 1 is configured to place a subject P to be irradiated with X-rays thereon. In a state in which the subject P is placed on the top board 1, the treatment tool 200 is inserted and X-ray imaging is performed. The top board 1 is configured to be movable by a top board moving unit (not shown).

The imaging unit 2 performs X-ray imaging by irradiating the subject P with X-rays. The imaging unit 2 includes an X-ray tube 21 and an X-ray detector 22. The X-ray tube 21 generates X-rays when a voltage is applied. The X-ray tube 21 emits X-rays to the subject P placed on the top board 1 and into which the treatment tool 200 has been inserted. Further, the X-ray detector 22 is provided with, for example, an FDP (Flat Panel Detector). The X-ray detector 22 is configured to detect X-rays emitted from the X-ray tube 21 and transmitted through the subject P. Further, the X-ray detector 22 outputs a detection signal based on the detected X-rays.

The moving unit 3 movably holds the X-ray tube 21 and the X-ray detector 22. More specifically, the moving unit 3 is provided on the ceiling C and supports the X-ray tube 21 and the X-ray detector 22 so as to face with each other across the top board 1 on which the subject P is placed. The moving unit 3 supports them so that the position and the angle of the imaging unit 2 with respect to the subject P can be changed. The moving unit 3 also supports the X-ray tube 21 and the X-ray detector 22 in such a manner that the distance between the X-ray tube 21 and the X-ray detector 22 can be changed. The moving unit 3 moves the imaging unit 2 to perform X-ray imaging from various positions and various angles relative to the subject P.

The display unit 4 is a monitor, such as, e.g., a liquid crystal display. The display unit 4 displays the images (still image and moving image) generated by the control unit 6.

The operation unit 5 is configured to accept an input operation for operating the X-ray imaging apparatus 100. Specifically, the operation unit 5 accepts an input operation for determining the quantity of X-rays to be emitted, the X-ray irradiation angle and the like when performing X-ray imaging on the subject P. The operation unit 5 receives the input operation for executing the control by the control unit 6.

The control unit 6 is a computer including a CPU (Central Processing Unit), a ROM (Read Only Memory), a RAM (Random Access Memory), etc. The control unit 6 functions as a control unit 6 for performing control of each part of the X-ray imaging apparatus 100, control of generating an X-ray image A, and control of image processing on the generated X-ray image by executing a predetermined control program by the CPU. The control by the control unit 6 will be described in detail later.

The storage unit 7 is configured by a storage device, such as, e.g., a hard disk drive. The storage unit 7 is configured to store image data, imaging conditions, and various set values. The storage unit 7 is storing a program for causing the control unit 6 to function.

(Control by Control Unit)

Figure 5:
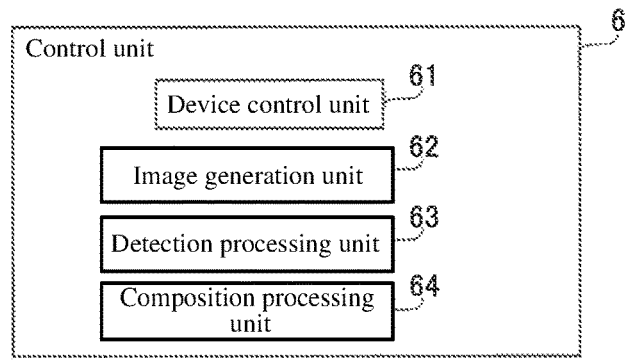
FIG. 5 is a diagram for explaining the functional configuration of the control unit according to the embodiment.

As shown in FIG. 5, the control unit 6 includes, as functional configurations, a device control unit 61, an image generation unit 62, a detection processing unit 63, and a composition processing unit 64. That is, the control unit 6 functions as the device control unit 61, the image generation unit 62, the detection processing unit 63, and the composition processing unit 64 by performing the program.

The device control unit 61 controls various parts of the X-ray imaging apparatus 100. For example, the device control unit 61 controls the imaging unit 2 to perform X-ray imaging. Then, it acquires the detection signal output by the X-ray detector 22. Further, the device control unit 61 performs the control for moving the moving unit 3. Further, the device control unit 61 acquires the operation signal based on the input operation received by the operation unit 5 and performs the control of each unit of the X-ray imaging apparatus 100 based on the acquired operation signal.

The image generation unit 62 generates, as shown in FIG. 3, an X-ray image A based on the detection signal output by the X-ray detector 22. The image generation unit 62 generates, based on the detection signal output by the X-ray detector 22, the X-ray image A in the form of a moving image. That is, X-rays are intermittently emitted to the subject P a plurality of times at predetermined time intervals by the X-ray tube 21. The X-ray detector 22 successively detects the X-rays intermittently emitted a plurality of times. The image generation unit 62 images the detection signal sequentially output from the X-ray detector 22 to generate a plurality of X-ray images A. That is, the image generation unit 62 successively generates n pieces of X-ray images A (A1, A2, . . . , An) (n is an integer).

Figure 6:
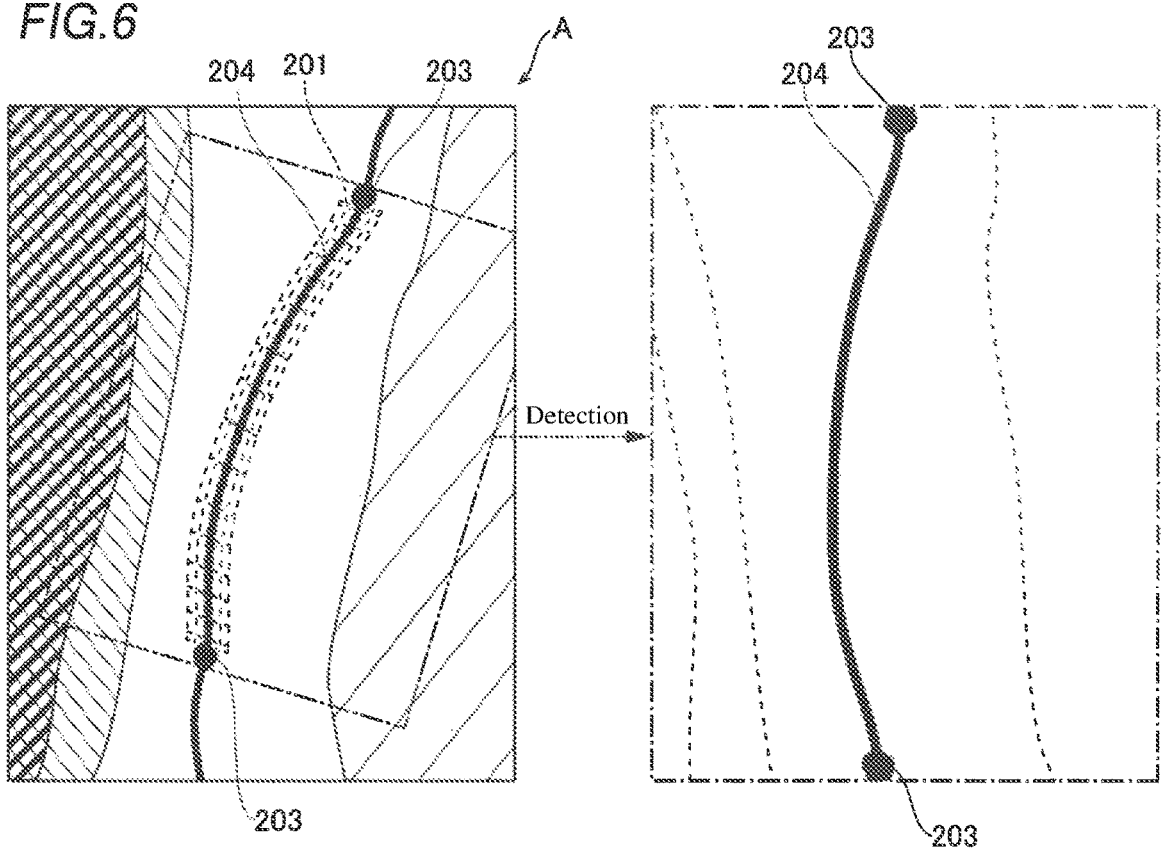
FIG. 6 is a diagram for explaining the detection of a marker and a guidewire according to the embodiment.

As shown in FIG. 6, the detection processing unit 63 detects, in the X-ray image A generated by the image generation unit 62, both of the marker 203 for indicating the position of the stent 201 to be indwelled in the body of the subject P and the guidewire 204 placed in the body of the subject P separately from the stent 201. Specifically, the detection processing unit 63 is configured to detect the position of the marker 203 for indicating the position of the stent 201 and the shape of at least a part of the guidewire 204

Figure 7:
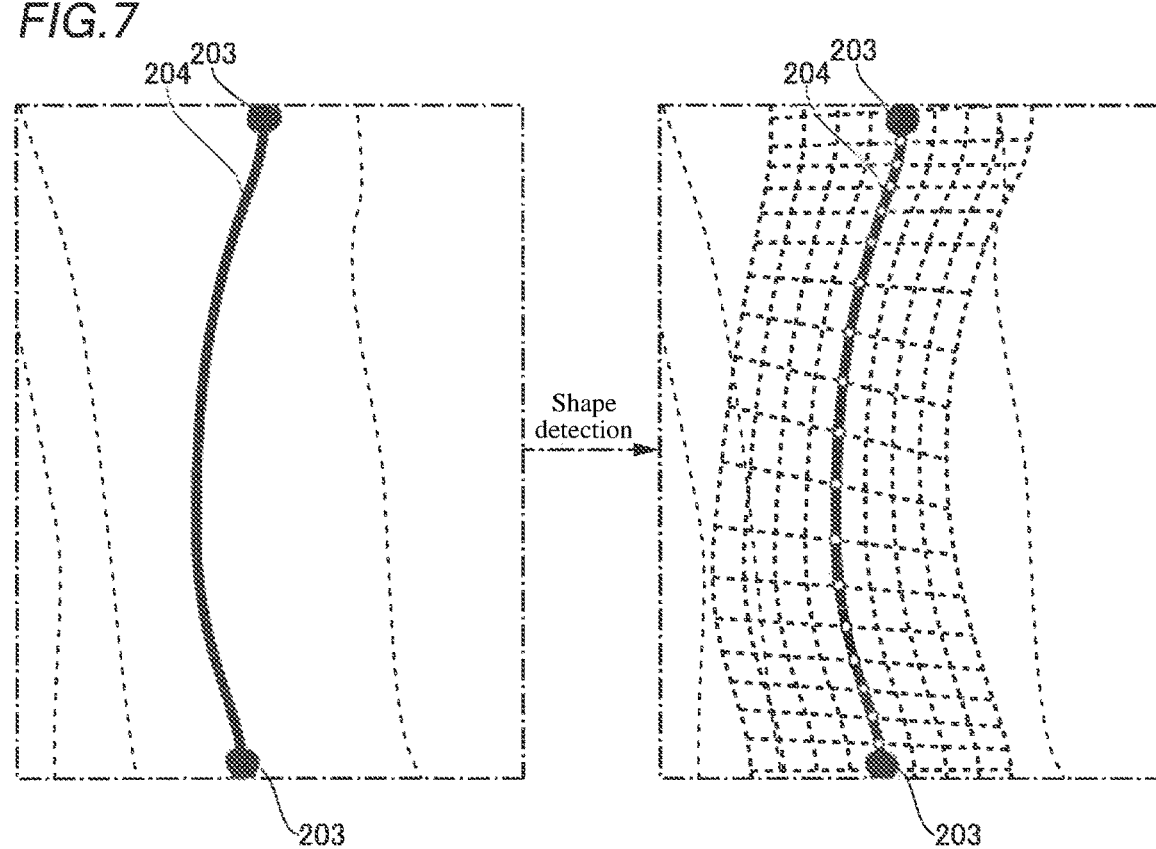
FIG. 7 is a diagram for explaining the detection of the shape of a guidewire according to the embodiment.

For example, the detection processing unit 63 performs filtering on the X-ray image A generated by the image generation unit 62. The detection processing unit 63 detects the position of the marker 203 provided at both ends of the stent 201 in the X-ray image A on which filtering has been performed. As shown in FIG. 7, the detection processing unit 63 detects the shape of the guidewire 204 (the degree of bending of the guidewire 204) which is positioned between the position of the marker 203 provided at one end of the stent 201 and the position of the marker 203 provided at the other end of the stent 201. That is, between the two markers 203, by extracting the feature quantity on the shape of the guidewire 204, the shape of the guidewire 204 in the X-ray image A is detected.

Figure 8:
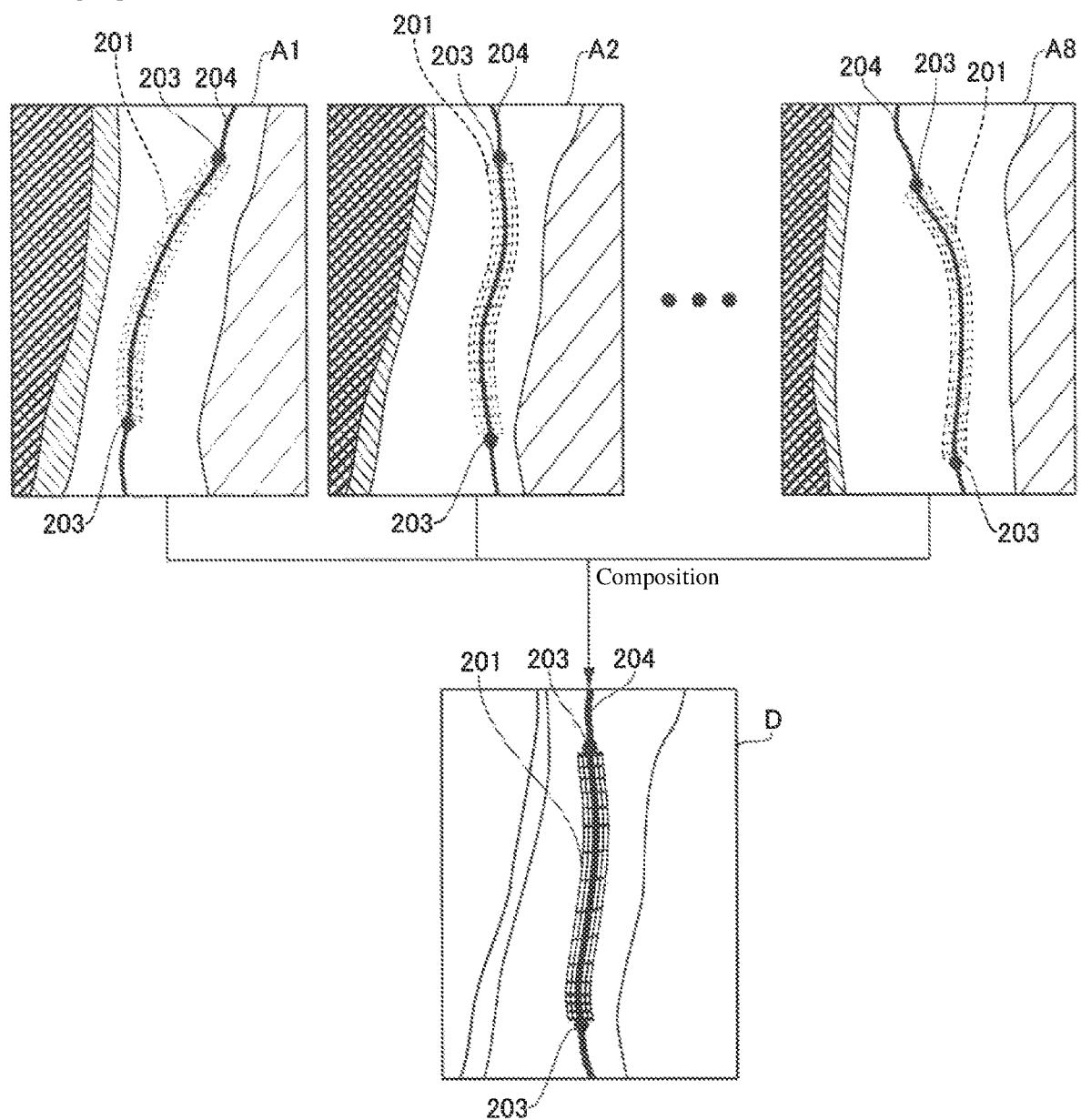
FIG. 8 is a diagram for explaining the generation of a composite image according to the embodiment.

The composition processing unit 64 generates a composite image D by superimposing a plurality of X-ray images A based on the marker 203 detected by the detection processing unit 63 and the detected guidewire 204, as shown in FIG. 8. Specifically, the composition processing unit 64 deforms each of the plurality of X-ray images A based on the detected position of the marker 203 and the detected shape of the guidewire 204, thereby generating a composite image D in such a manner that the markers 203 and the guidewires 204 overlap with each other.

The composition processing unit 64 is configured to generate the composite image D by superimposing the plurality of X-ray images A in such a manner that the markers 203 overlap at the marker reference positions Mα (see FIG. 9 and FIG. 10) acquired based on the positions of the plurality of markers 203 detected in each of the plurality of X-ray images A and the guidewires 204 are overlapped with the guidewire reference shape Gα (see FIG. 11 and FIG. 12) acquired based on the shapes of the plurality of guidewires 204 each detected in each of the plurality of X-ray images A. The guidewire reference shape Gα is an example of the "device reference shape" recited in claims.

In this embodiment, the marker reference position Mα is the average position of the markers 203 detected in the plurality of X-ray image A, and the guidewire reference shape Gα is the average shape of the guidewires 204 detected in the plurality of X-ray image A. The composition processing unit 64 acquires the coordinate indicating the position of the marker 203 detected in each of the plurality of X-ray images A. Then, based on the coordinates of the markers 203 in the plurality of X-ray images A, the coordinate to be averaged is acquired as the marker reference position Mα. The composition processing unit 64 extracts the guidewire 204 detected in each of the plurality of X-ray images A as one curved line. Further, the composition processing unit 64 extracts the feature quantity of the detected guidewire 204. The composition processing unit 64 acquires the guidewire reference shape Gα based on the average of the extracted feature quantities.

As shown in FIG. 8, the composition processing unit 64 composes, for example, eight pieces of X-ray images A (A1, A2, ..., A8) to generate the composite image D which is an image in which the stent 201 is emphasized. Eight pieces of X-ray images A (A1, A2, ..., A8) are X-ray images A successively generated by the image generation unit 62.

Figure 9:
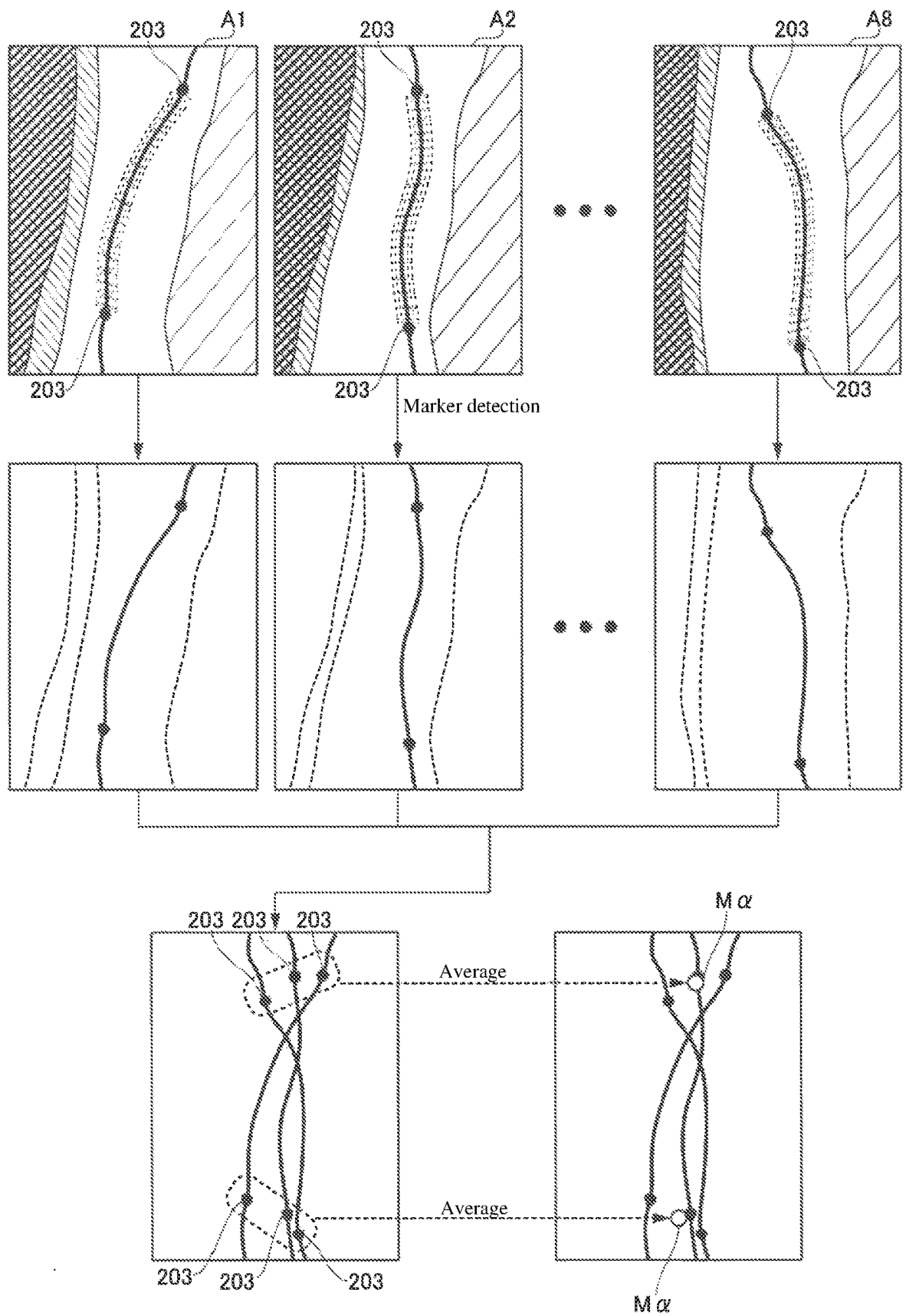
FIG. 9 is a diagram for explaining a marker reference position according to an embodiment.
Figure 10:
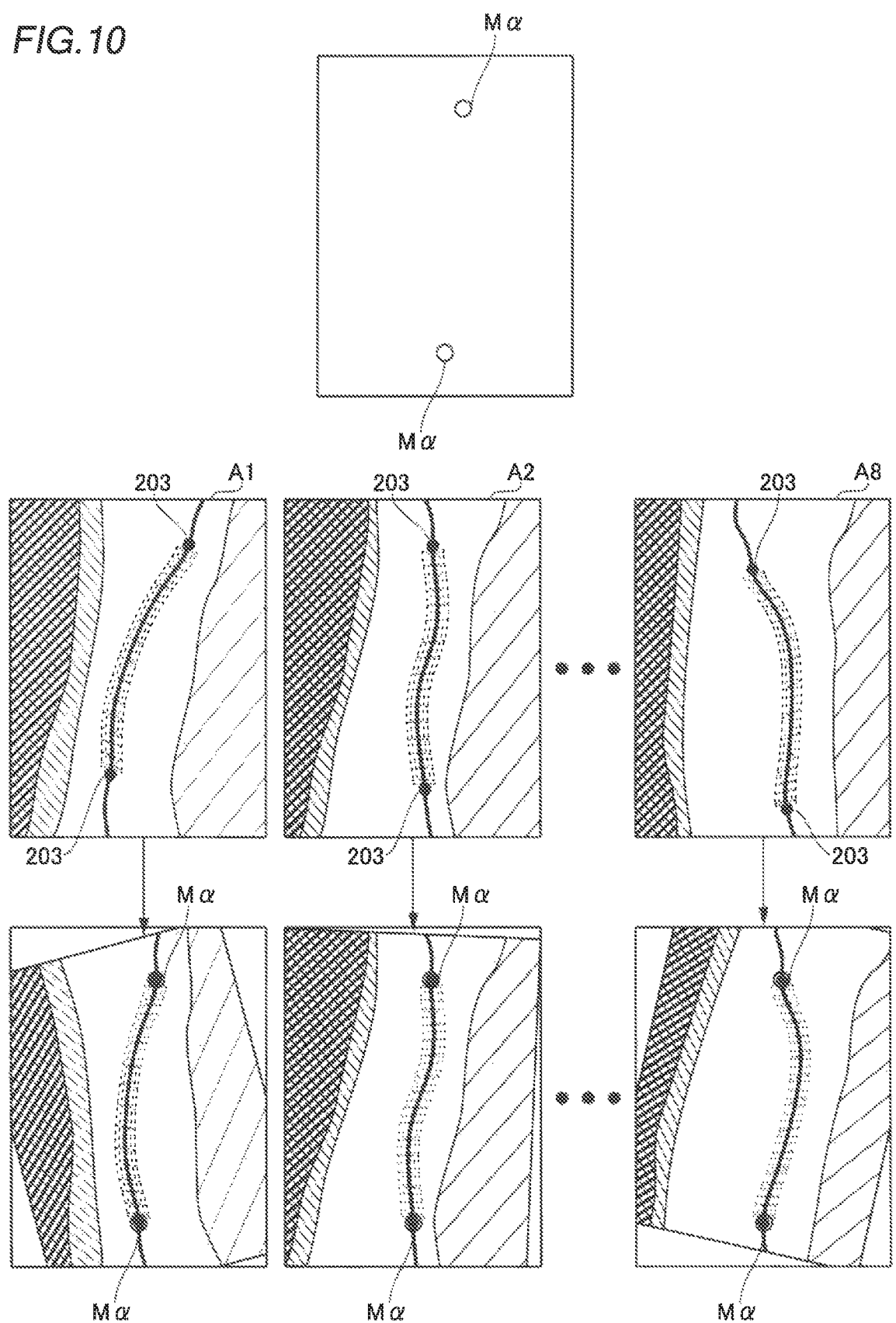
FIG. 10 is a diagram for explaining a variation of an X-ray image based on a marker reference position according to one embodiment.

As shown in FIG. 9, the composition processing unit 64 acquires the coordinate of the average of the coordinates of the markers 203 detected in eight pieces of X-ray images A1 to A8 as a marker reference position Mα. Then, as shown in FIG. 10, in the eight pieces of X-ray images A, the composition processing unit 64 deforms each of the eight pieces of the X-ray images A in such a manner that the markers 203 overlap with the marker reference position Mα.

Figure 11:
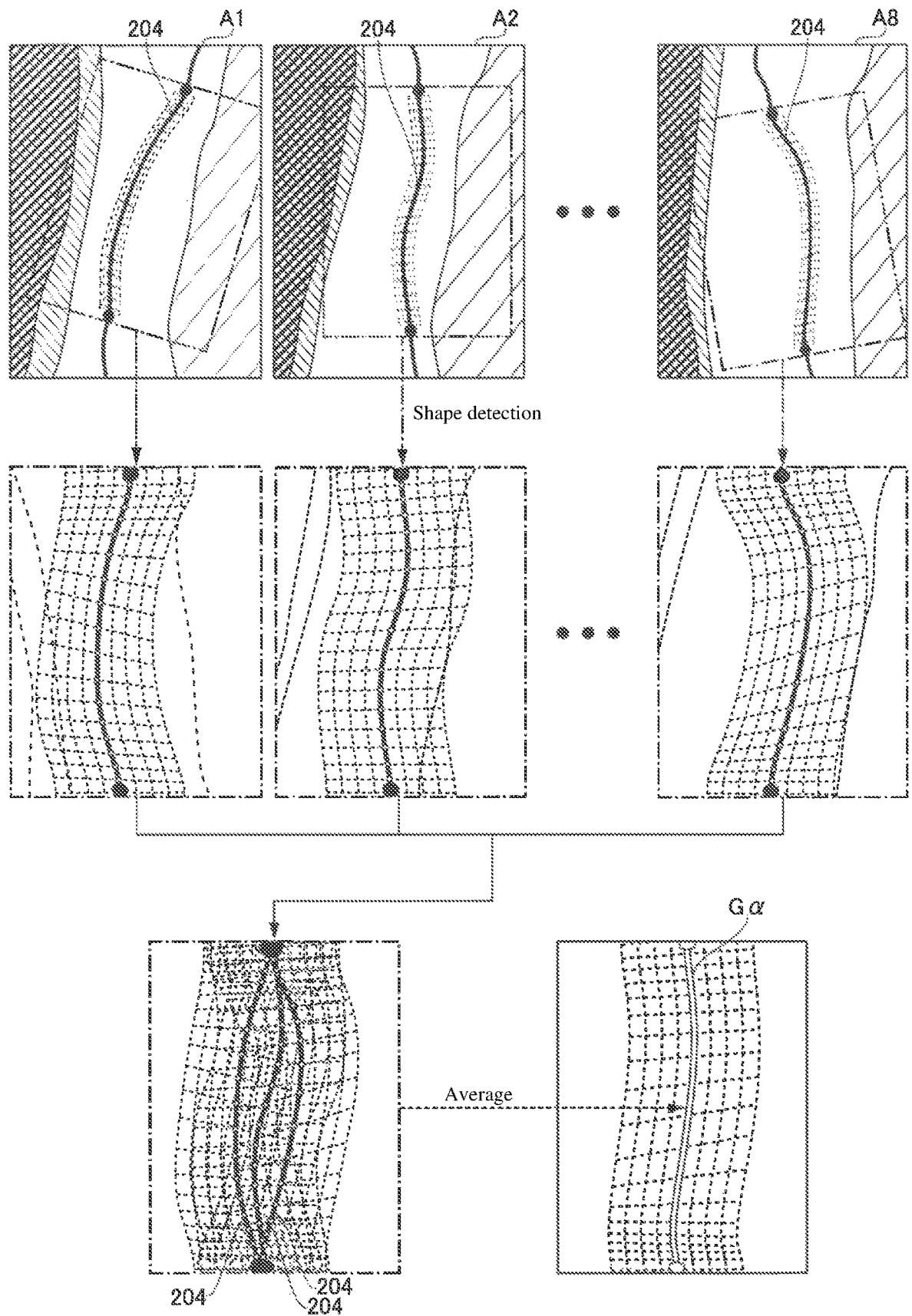
FIG. 11 is a diagram for explaining a guidewire reference shape according to an embodiment.
Figure 12:
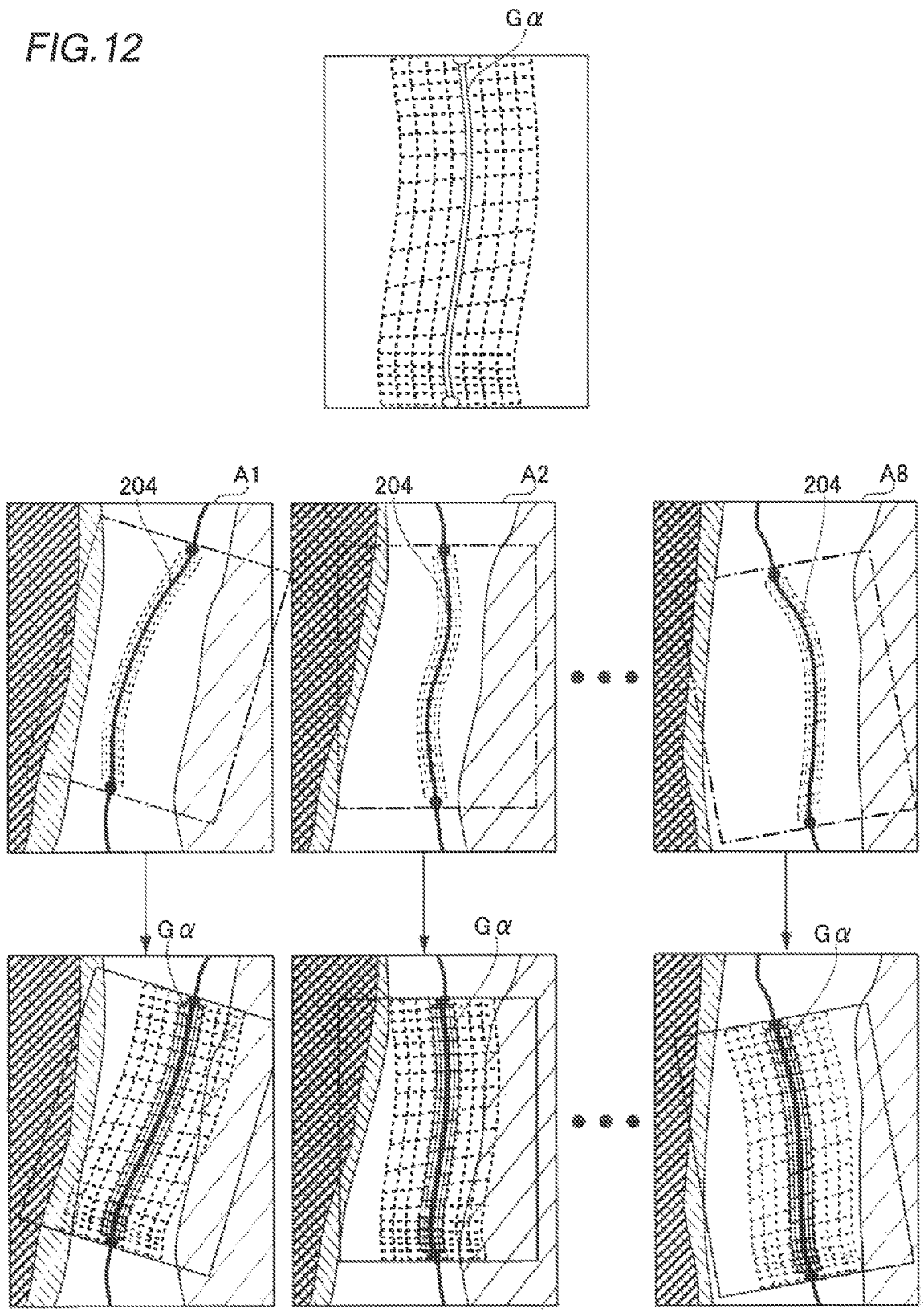
FIG. 12 is a diagram for explaining a variation of an X-ray image based on the guidewire reference shape according to one embodiment.

Further, as shown in FIG. 11, the composition processing unit 64 acquires the average shape of the guidewires 204 in the eight pieces of the X-ray images A as a guidewire reference shape Gα from the feature quantity extracted based on the shape of the guidewire 204 detected in each of the eight pieces of X-ray images A. The guide wire reference shape Gα is a shape acquired by averaging the extracted feature quantities for the guidewires 204 for the eight pieces of the X-ray images A. Then, as shown in FIG. 12, the composition processing unit 64 deforms each of the eight pieces of the X-ray images A in such a manner that the guidewire 204 of in each of the eight pieces of the X-ray images A overlap with the acquired guidewire reference shape Gα.

In this manner, the composition processing unit 64 generates the composite image D in which the stent 201 is highlighted by superimposing the plurality of X-ray images A in such a manner that the markers 203 detected in the plurality of X-ray images A overlap with each other and the guidewires 204 detected in the plurality of X-ray images A overlap with each other.

Figure 13:
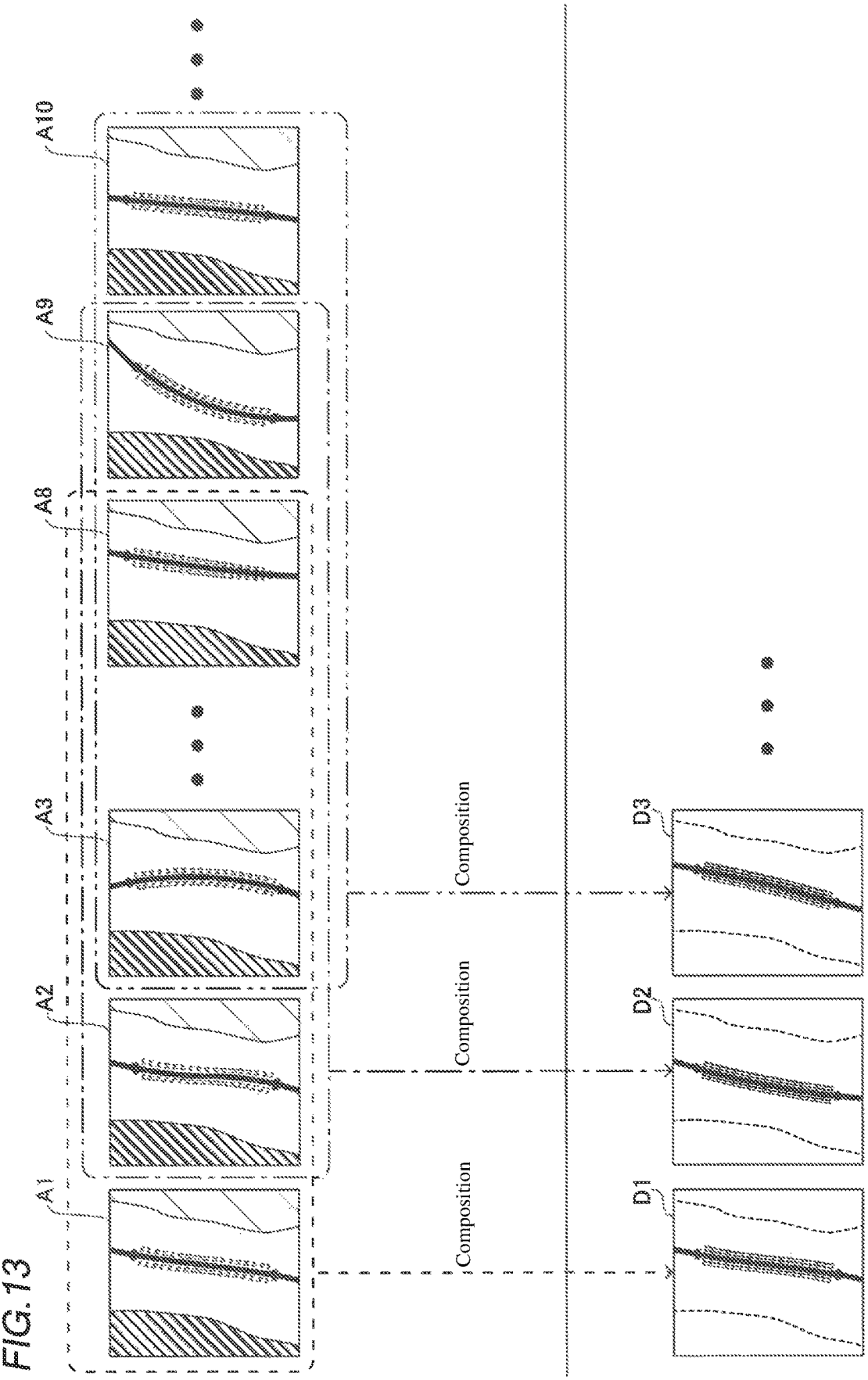
FIG. 13 is a diagram for explaining the generation of a plurality of composite images by one embodiment.

Further, as shown in FIG. 13, the composition processing unit 64 generates a plurality of composite images D (D1, D2, D3, ...) based on the plurality of X-ray images A generated successively. The composition processing unit 64 composes eight pieces of X-ray images A (A1 to A8) successively generated by the image generation unit 62 to generate the composite image D1. Then, the composite image D2 is generated by composing successively generated X-ray images A2 to A9.

Similarly, the composition processing unit 64 composes successively generated X-ray images An to An+7 to generate a composite image Dn. In this manner, the composition processing unit 64 successively deforms the successively generated X-ray images A and successively generates composite images D (D1, D2, ..., Dn). Thus, the composite image D1 is generated based on the position of the marker 203 and the shape of the guidewire 204 detected in each of the X-ray images A1 to A8. The composite image D2 is then generated based on the position of the marker 203 and the shape of the guidewire 204 detected in each of the X-ray images A2 to A9. Similarly, the composite image Dn is generated based on the position of the marker 203 and the shape of the guidewire 204 detected in each of the X-ray images An to An+7.

Then, the composition processing unit 64 generates a plurality of composite images D to generate a moving image using the generated plurality of composite images D. Specifically, the composition processing unit 64 is configured to overlap a predetermined number of successively generated X-ray images A to generate a composite image D and causes the display unit 4 to successively display the plurality of generated composite images D to display the composite image D as a moving image. That is, the composition processing unit 64 successively composes the successively generated X-ray images A (A1 to An) to generate a plurality of composite images D (D1 to Dn−7) and generates a moving image based on the generated composite images D1 to Dn−7. And the composition processing unit 64 causes the display unit 4 to display the generated moving image. In this manner, the composition processing unit 64 causes the display unit 4 to display the image in which the stent 201 is highlighted as a moving image image.

(X-Ray Image Processing Method)

Figure 14:
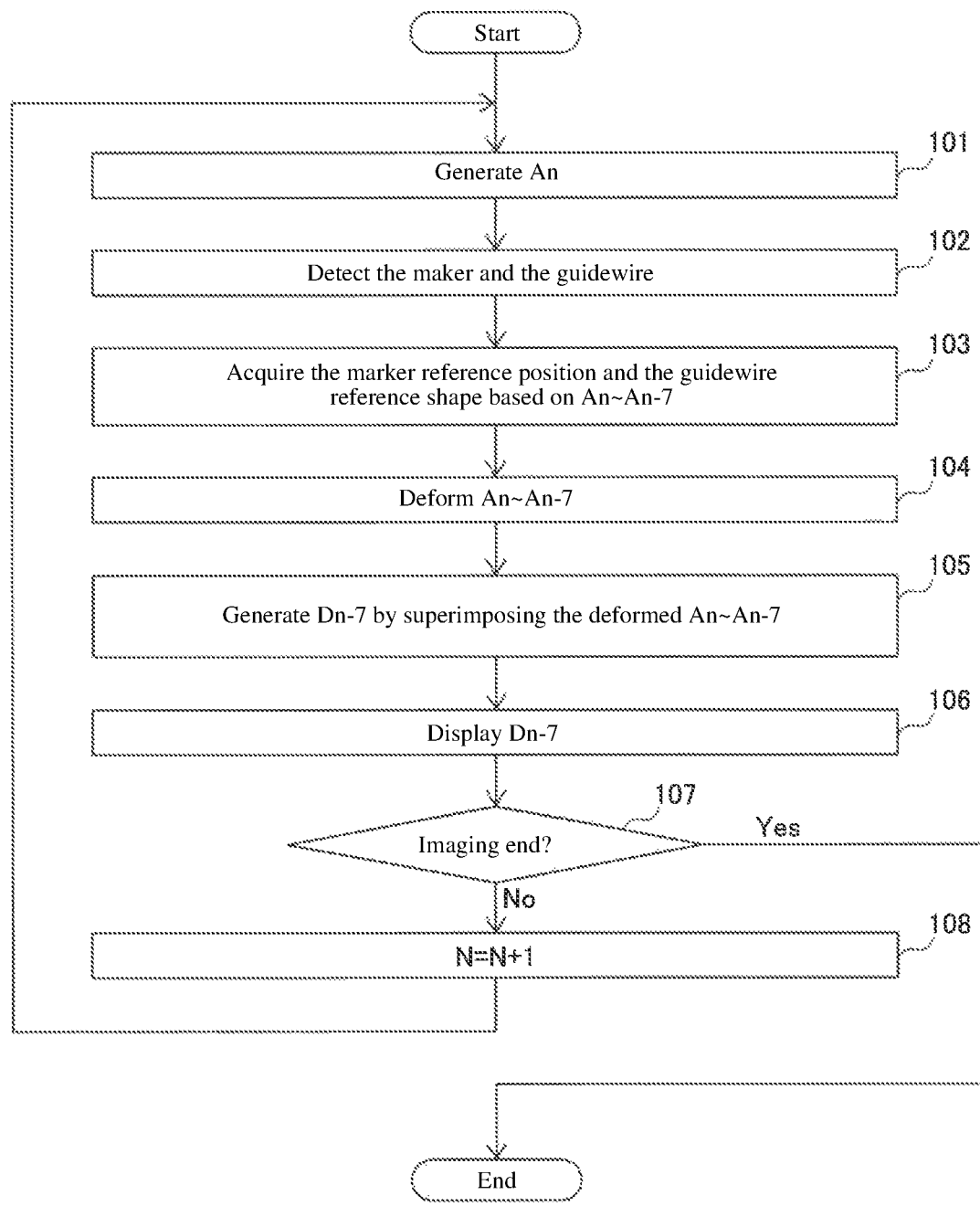
FIG. 14 is a flowchart for explaining an X-ray image processing method according to an embodiment.

Next, with reference to FIG. 14, the X-ray image processing method using the X-ray imaging apparatus 100 according to this embodiment.

First, in Step 101, X-rays are successively emitted to the subject P into which the treatment tool 200 has been inserted, at predetermined intervals. An X-ray image A (A1, A2, ..., An) is continuously generated by detecting the X-rays transmitted through the subject P.

Next, in Step 102, in the generated X-ray image A, both of the marker 203 for indicating the position of the stent 201 to be indwelled in the body of the subject P and the guidewire 204 to be placed in the body of the subject P separately from the stent 201 are detected.

Next, in Step 103, the marker reference position Ma and the guidewire reference shape Gα are acquired based on the position of the marker 203 and the shape of the guidewire 204 in each of the successively generated predetermined numbers (e.g., eight) of X-ray images A (An−7 to An).

Next, in Step 104, each of successively generated X-ray images A (An−7 to An) is deformed in such a manner that the markers detected in the X-ray images A (An−7 to An) overlap at the marker reference position Ma and the guidewires 204 detected in the X-ray images A (An−7 to An) overlaps with the guidewire reference shape Gα.

Next, in Step 105, deformed X-ray images A (An−7 to An) are superimposed to generate a composite image Dn−7.

Next, in Step 106, the generated composite image Dn−7 is displayed on the display unit 4.

Next, in Step 107, it is determined whether or not X-ray imaging has been completed based on whether or not an input operation relating to the end of imaging has been performed for the operation unit 5. When it is determined that X-ray imaging has not been completed, N is incremented (n=n+1) in Step 108 to return to Step 101 and a new X-ray image An is generated by the image generation unit 62. When it is determined that X-ray imaging has been completed, the control flows are finished.

Effects of this Embodiment

In this embodiment, the following effects can be obtained.

In the X-ray imaging apparatus 100 of this embodiment, as described above, in the generated X-ray image A, the marker 203 for indicating the position of the predetermined target object (stent 201) to be indwelled in the body of the subject P and the device (guidewire) to be placed in the body of the subject P separately from the stent 201 are both detected. Then, a composite image D is generated by superimposing a plurality of X-ray images A based on the detected marker 203 and the detected guidewire 204.

With this, in the generated X-ray image A, the position of the stent 201 in the body of the subject P can be specified by detecting the marker 203. Further, in the generated X-ray image A, by detecting the guidewire 204 placed in the body of the subject P, it is possible to detect the change in the position and the shape of the guidewire 204 due to the the movements in the body of the subject P in each of the generated X-ray images A. Therefore, in each of the generated X-ray images A, the movements in the body of the subject P can be specified indirectly, so that the change in the shape of the stent 201 placed in the body of the subject P can be specified indirectly.

Then, in this embodiment, by detecting both of the marker 203 and the guidewire 204, it is possible to specify the relative position and the relative shape of the subject P relative to the marker 203 of the stent 201 in the body of the subject. Therefore, when superimposing the plurality of X-ray images, the plurality of X-ray images A can be superimposed with each other so as to reduce blurring based on the position and the shape of the stent 201 reflected in each of the plurality of X-ray images A. As a result, even when the shape of the stent 201 is different in each of the plurality of X-ray images A, the visibility of the stent 201 can be improved in the composite image D generated by superimposing the plurality of X-ray images A.

Further, in the above-described embodiment, further effects can be acquired by the following configuration.

That is, in this embodiment, as described above, the composition processing unit 64 is configured to generate the composite image D by superimposing the plurality of X-ray images A in such a manner that the markers 203 each detected in each of the plurality of X-ray images A overlap with each other and the devices (guidewires 204) each detected in the plurality of X-ray images A overlaps with each other.

With this configuration, the plurality of X-ray image A can be superimposed in such a manner that the markers 203 each detected in each of the plurality of X-ray images A overlaps with each other and the guidewires 204 each detected in each of the plurality of X-ray images A overlap with each other. Therefore, even when the shapes of the X-ray images A in the plurality of guidewires 204 differ, it is possible to superimpose the plurality of X-ray images A in such a manner that the guidewires 204 overlap with each other.

That is, the plurality of X-ray images A can be superimposed to cope with the changes in the position and the shape of the body of the subject P in each of the plurality of X-ray images A. As a result, even in cases where the shapes of the stents 201 differ depending on the movements of the subject P in the body (pulsations of the heart or the like) in the plurality of X-ray images A, it is possible to generate the composite image D in such a manner that the stents 201 in the plurality of X-ray images A overlap (blurring is reduced). Therefore, the visibility of the stent 201 can be further improved in the generated composite image D.

Further, in this embodiment, as described above, the detection processing unit 63 is configured to detect the position of the marker 203 and the shape of the device (guidewire 204). The composition processing unit 64 is configured to generate the composite image D by superimposing the plurality of X-ray images A in such a manner that the markers 203 overlap with each other and the guidewires 204 overlap with each other by deforming each of the plurality of X-ray images A based on the position of the detected marker 203 and the shape of the detected guidewire 204.

With this configuration, it is possible to cause the positions of the markers 203 to overlap with each other based on the positions of the markers 203 detected in the plurality of X-ray images A and also possible to deform each of the X-ray images A in such a manner that the shapes of the guidewires 204 overlap based on the shapes of the guidewires 204 detected in the plurality of X-ray images A. Therefore, even when the position and the shape of the stent 201 differ in each of the plurality of X-ray images A, the composite image D can be generated in such a manner that the stents 201 overlap with each other by deforming each of the plurality of X-ray images A in such a manner that the marker 203 and the guidewire 204 overlap. Consequently, when composing the composite image D, it is possible to superimpose the stents 201 in the plurality of X-ray images A more accurately.

Further, in this embodiment, as described above, it is configured in such a manner that the device (guidewire 204) is positioned in the body of the subject P integrally with the predetermined target object (stent 201) and the detection processing unit 63 detects the marker 203 and the guidewire 204 which changes in the shape integrally with the stent 201 in the body of subject P. By configuring as described above, the guidewire 204 which changes in the shape integrally with the stent 201 is detected in the X-ray image A, and therefore the shape of the stent 201 can be detected by detecting the shape of the guidewire 204.

With this, by superimposing the X-ray images A in such a manner that the detected guidewires 204 overlap with each other, it is possible to superimpose the X-ray images A in such a manner that the stents 201 overlap with each other. Consequently, in the generated composite image D, the stents 201 can be superimposed with each other more accurately. Thus, the stent 201 can be more clearly emphasized (blurring is reduced)

Further, in this embodiment, as described above, the predetermined target object includes the stent 201 to be indwelled in the body of the subject P. The device includes the guidewire 204 used for indwelling the stent 201 in the subject P. The detection processing unit 63 is configured to detect the position of the marker 203 for indicating the position of the stent 201 and the shape of at least a part of the guidewire 204 to indicate the position of the 201. The composition processing unit 64 is configured to generate the composite image D by superimposing the plurality of X-ray images A based on the position of the marker 203 and the shape of at least a part of the detected guidewire 204.

Here, the stent 201 is provided integrally with the guidewire 204. Therefore, by detecting the change in the shape of the guidewire 204 in the body of the subject P, it is possible to detect the change in the shape of the stent 201 in the body of the subject P. Considering this, as in this embodiment, by configuring in such a manner that the composition processing unit 64 generates the composite image D by superimposing the plurality of X-ray images A based on the detected position of the marker 203 and the detected shape of at least a part of the guidewire 204, based on the position of the detected marker 203 and the position of the detected guidewire 204, it is possible to generate the composite image D in such a manner that the stents 201 in the plurality of X-ray images overlap with each other. As a result, in the composite image D, since the superimposed stents 201 are displayed in an emphasized manner, the visibility of the stent 201 can be improved.

Further, in this embodiment, as described above, the marker 203 is provided at each of both ends of the stent 201 to indicate the position of the stent 201, and the detection processing unit 63 is configured to detect the position of the marker 203 provided at both ends of the stent 201 and to detect the shape of the guidewire 204 position between the position of the marker 203 provided at one end of the stent 201 and the position of the marker 203 provided at the other end of the stent 201.

With this configuration, it is possible to detect the shape of the guidewire 204 positioned between one end of the stent 201 and the other end thereof. Therefore, it is possible to detect only the shape of the part of the guidewire 204 where the stent 201 is arranged out of the entire guidewire 204. As a result, in each of the plurality of X-ray images A, it is possible to detect the position and the shape of the stent 201 with high accuracy when superimposing the plurality of X-ray images A.

Further, in this embodiment, as described above, the detection processing unit 63 is configured to detect the position of the marker 203 and the shape of the device (guidewire 204). The composition processing unit 64 is configured to generate the composite image D by superimposing the plurality of X-ray images A in such a manner that the markers 203 overlap at the marker reference position $M\alpha$ acquired based on the position of the plurality of composite images 203 detected in the plurality of X-ray images A, and the guidewires 204 overlap with the device reference shape (guidewire reference shape $G\alpha$) acquired based on the shapes of the plurality of guidewires 204 detected in the plurality of X-ray images A.

By configuring as described above, it is possible to overlap the markers 203 at the marker reference shape $G\alpha$ and superimpose the guidewire reference shape $G\alpha$ and the guidewire 204. Therefore, based on the certain marker reference position $M\alpha$ and a certain constant guidewire reference shape $G\alpha$, it is possible to superimpose the plurality of X-ray images A.

Therefore, in a case where the plurality of composite images D is sequentially generated by superimposing a predetermined number (for example, 8 pieces) of X-ray images A among the plurality of continuously generated X-ray images A, the plurality of composite images D can be generated in such a manner that the position and the shape of the stent 201 in the plurality of generated composite images D becomes a predetermined position and shape based on the marker reference position $M\alpha$ and the guidewire reference shape $G\alpha$. As a result, it is possible to suppress the decrease in visibility due to the difference in the position of the stent 201 in each of the plurality of composite images D generated, as compared with the case where a reference at the time of superimposing them is not provided.

Further, in this embodiment, as described above, the marker reference position $M\alpha$ is the average position of the markers detected in the plurality of X-ray images A. The device reference shape (guidewire reference shape $G\alpha$) is the average shape of the shapes of the devices (guidewire 204) detected in each of the plurality of X-ray images A. The composition processing unit 64 is configured to generate the composite image D by superimposing the plurality of X-ray images A in such a manner that the markers 203 each detected in each of the plurality of X-ray images A overlap with each other at the marker reference position $M\alpha$ and the guidewires 204 each detected in each of the plurality of X-ray images A overlap with the guidewire reference shape $G\alpha$.

Here, when generating a moving image based on a plurality of composite images D generated by superimposing a predetermined number of X-ray images A, the position of the stent 201 in the moving image (composite image D) may vary significantly from frame to frame due to the change in the position at which the markers 203 overlap with each other.

Further, similarly, in a case where the shape of the reference of the guidewire 204 changes for each frame (for each composite image D), the shape of the stent 201 in the moving image may significantly change for each frame (for each composite image D).

In contrast, in this embodiment, the marker reference position $M\alpha$ is the average position of the markers each detected in each of the plurality of X-ray images A. The device reference shape (guidewire reference shape $G\alpha$) is the average shape of the shapes of the devices (guidewires 204) each detected in each of the plurality of X-ray images A. With this configuration, even in a case where a moving image is generated using the plurality of composite images D, the marker reference position $M\alpha$ and the guidewire reference shape $G\alpha$ do not significantly change from frame to frame. Therefore, in each of the plurality of composite images D, it is possible to suppress the significant change in the position and the shape of the stent 201. As a result, it is possible to effectively suppress the decrease in visibility due to the significant change in the position and the shape of the stent 201 when generating a moving image using a plurality of composite images D.

Also, in this embodiment, as described above, the composition processing unit 64 is configured to generate a composite image D by superimposing a predetermined number of continuously generated X-ray images A and display the composite image D as a moving image by successively displaying the plurality of generated composite images D. With this configuration, it is possible to display the composite image D generated so as to improve the visibility of the stent 201 as a moving image based on the successively generated X-ray images A.

Therefore, when generating an X-ray image A sequentially in real time, the composite image D improved in the visibility of the stent 201 can be similarly displayed as a moving image in real time. As a result, it is possible to clearly display the stent 201 in real time when performing the procedure while visually checking the position and the shape of the stent 201.

(Effects of X-Ray Image Processing Method by this Embodiment)

In the X-ray image processing method of this embodiment, the following effects can be obtained.

In the X-ray image processing method of the embodiment, by configuring as described above, in the generated X-ray image A, both of the marker 203 for indicating the position of the predetermined target object (stent 201) to be indwelled in the body of the subject P and the device (guidewire 204) to be arranged in the body of the subject P separately from the stent 201 can be detected. Then, the composite image D is generated by superimposing the plurality of X-ray images A based on the detected marker 203 and the detected guidewire 204. Thus, in the generated X-ray image A, the position of the stent 201 in the body of the subject P can be acquired by detecting the marker 203.

Further, in the generated X-ray image A, by detecting the guidewire 204 to be arranged in the body of the subject P, it is possible to detect the change in the position and the shape of the guidewire 204 due to the movements of the subject P in each of the generated X-ray images A. Therefore, in each of the generated X-ray images A, the movements in the body of the subject P can be acquired indirectly, so that the change in the shape of the stent 201 to be indwelled in the body of the subject P can be acquired indirectly.

Further, in this embodiment, by detecting both of the marker 203 and the guidewire 204, it is possible to acquire the relative position and the relative shape of the subject P with the marker 203 of the stent 201 in the body. Therefore, when superimposing a plurality of X-ray images A, the plurality of X-ray images A can be superimposed with each other so as to reduce blurring based on the positions and the shapes of the stents 201 each contained in each of the plurality of X-ray images A. As a result, even in a case where the shape of the stent 201 is different in each of the plurality of X-ray images A, the visibility of the stent 201 can be improved in the composite image D generated by superimposing the plurality of X-ray images A.

(Modifications)

It should be understood that the embodiments disclosed here are examples in all respects and are not restrictive. The scope of the present invention is shown by the claims rather than the descriptions of the embodiments described above, and includes all changes (modifications) within the meaning of equivalent and claims.

For example, in the above-described embodiment, an example is shown in which the composition processing unit 64 is configured to generate a composite image D by superimposing a plurality of X-ray images A in such a manner that the markers 203 each detected in each of the plurality of X-ray images A overlap with each other and the devices (guidewires 204) each detected in each of the plurality of X-ray images A overlap, but the present invention is not limited thereto.

For example, a certain threshold value may be provided, and a plurality of X-ray images A may be superimposed in such a manner that the detected markers 203 are separated from each other by a value distance smaller than the threshold value distance. That is, even if the markers 203 do not accurately overlap, a plurality of X-ray images A may be superimposed so as to be closer than a certain distance.

In the above-described embodiment, the detection processing unit 63 is configured to detect the position of the marker 203 and the shape of the device (guidewire 204) of the marker 203. An example is shown in which the composition processing unit 64 is configured to generate a composite image D by superimposing a plurality of X-ray images A in such a manner that the markers 203 overlap with each other and the guidewires 204 overlaps with each other by deforming each of the plurality of X-ray images A based on the detected position of the marker 203 and the detected shape of the guidewire 204, but the present invention is not limited thereto.

Figure 15:
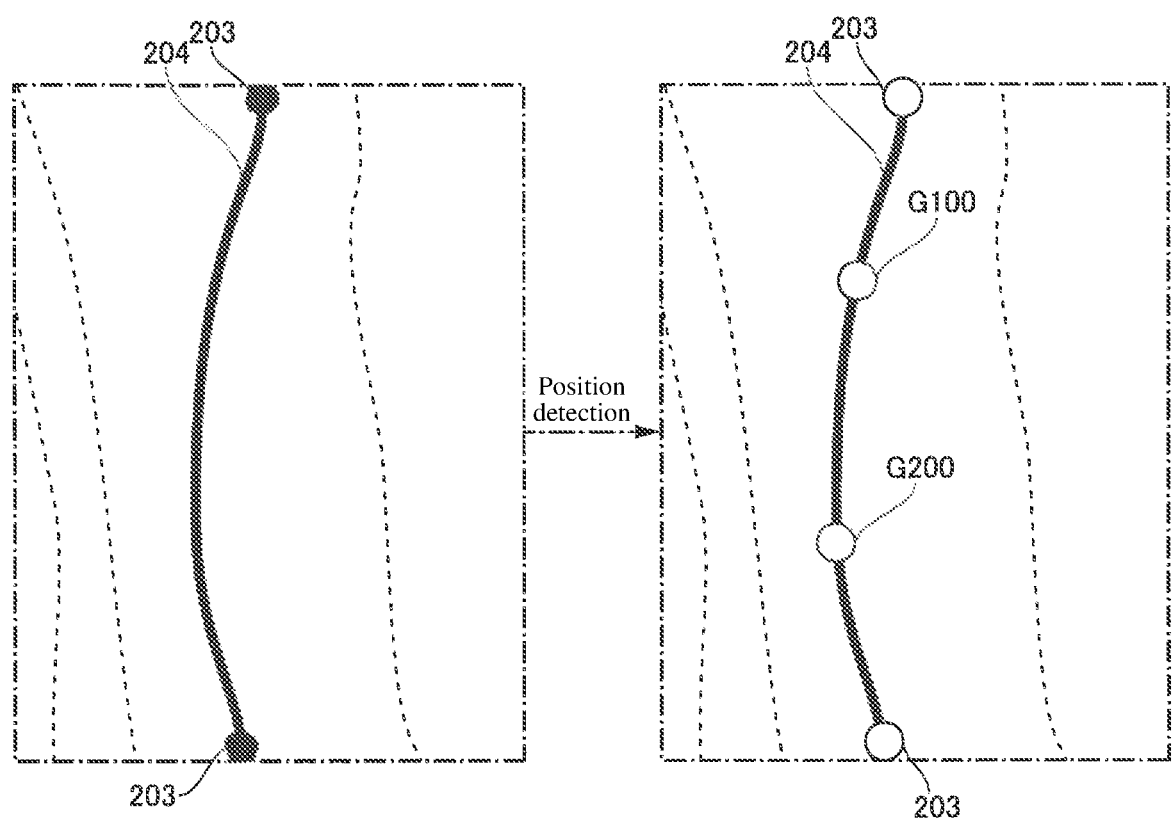
FIG. 15 is a diagram for explaining the detection position of the guidewire according to a modification of one embodiment.

For example, rather than detecting the shape of the guidewire 204, it may be configured to detect the coordinate indicating the position of the guidewire 204 in the X-ray image A. That is, as shown in FIG. 15, for example, the coordinates of the markers 203 arranged at both ends of the stent 201 and two points (coordinates G100 and G200) of the guidewire 204 between both ends of the stent 201 may be detected. Then, the composite image D may be generated in such a manner that the detected positions of the marker 203 and the detected positions of the guidewire 204 overlap in the plurality of X-ray images A.

In the above-described embodiment, an example is shown in which it is configured in such a manner that the device (guidewire 204) is arranged in the body of the subject P integrally with a predetermined target object (stent 201) and the detection processing unit 63 detects the marker 203 and the guidewire 204 which change its shape integrally with the stent 201 in the body of the subject P, but the present invention is not limited thereto. For example, the device to be arranged in the body of the subject P may be a device not arranged in the body of the subject P integrally with the stent 201 Specifically, a stent may be indwelled in the body of the subject P separately from the stent 201.

In the above-described embodiment, an example is shown in which the predetermined target object includes a stent 201 to be indwelled in a body of a subject P, the device includes a guidewire 204 used to indwell the stent 201 in the subject P, the detection processing unit 63 is configured to detect the position of the marker 203 for indicating the position of the stent 201 and the shape of at least a part of the guidewire 204, and the composition processing unit 64 is configured to generate a composite image D by superimposing a plurality of X-ray images A based on the position of the detected marker 203 and the shape of at least a part of the detected guidewire 204, but the present invention is not limited thereto.

For example, as the predetermined target object, those other than the stent 201 may be targeted. In other words, the predetermined target object may include a prosthetic valve or the like to be indwelled in the blood vessel of the subject P. As the device, a device other than the guidewire 204 may be used. In other words, the device may include a balloon catheter and the like.

In addition, in the above-described embodiment, an example is shown in which the marker 203 is arranged at each of both ends of the stent 201 in order to indicate the position of the stent 201, and the detection processing unit 63 is configured to detect the position of the markers 203 arranged at both ends of the stent 201 and detect the shape of the guidewire 204 positioned between the position of the marker 203 provided at one end of the stent 201 and the position of the marker 203 provided at the other end of the stent 201, but the present invention is not limited thereto.

For example, the marker 203 may be provided at the center of the stent 201 in addition to both ends of the stent 201. A plurality of markers 203 may be provided at each of both ends of the stent 201. Further, the marker 203 may be provided outside both ends of the stent 201 The detection processing unit 63 may detect the shape of the entire guidewire 204 in the X-ray image A.

In the above-described embodiment, an example is shown in which the detection processing unit 63 is configured to detect the position of the marker 203 and the shape of the device (guidewire 204), and the composition processing unit 64 is configured to generate a composite image D by superimposing a plurality of X-ray images A in such a manner that the markers 203 overlap with each other at the marker reference position Mα acquired based on positions of the plurality of composite images 203 detected in the plurality of X-ray image A and the guidewire 204 overlaps with the device reference shape (guidewire reference shape Gα) acquired based on the shape of the plurality of guidewires 204 detected in each of the plurality of X-ray images A, but the present invention is not limited thereto.

For example, the predetermined coordinate in the X-ray image A may be the marker reference position Mα. Further, the predetermined shape may be the guidewire reference shape Gα. That is, the guidewire reference shape Gα is determined in advance as a straight line (rectangular), and the X-ray image A may be deformed in such a manner that the detected guidewire 204 of the X-ray image A overlaps with the predetermined straight line (rectangular).

In the above-described embodiment, an example is shown in which the composition processing unit 64 is configured to generate the composite image D by superimposing the plurality of X-ray images A in such a manner that the marker reference position Mα is the average of the markers each detected in each of the plurality of X-ray images A, the device reference shape (guidewire reference shape Gα) is the average shape of the devices (guidewires) each detected in each of the plurality of X-ray images A, and the composition processing unit 64 is configured to generate the composite image D by superimposing a plurality of X-ray images A in such a manner that the markers 203 each detected in each of the plurality of X-ray images A overlap with the marker reference position Mα and the guidewires 204 each detected in each of the plurality of X-ray images A overlaps with the guidewire reference shape Gα.

For example, the position of the marker 203 in the most recent X-ray image A among a plurality of X-ray images A may be set as the marker reference position Mα. Similarly, the shape of the guidewire 204 in the most recent X-ray image A of the plurality of X-ray images A may be set as the guidewire reference shape Gα. Note that the latest X-ray image A means an X-ray image A generated most lately (most newly) among a plurality of X-ray images A used in generating the composite image D. Further, the marker reference position Mα and the guidewire reference shape Gα may be acquired based on the median value rather than the average value.

In the above-described embodiment, an example is shown in which the composition processing unit 64 is configured to generate the composite image D by superimposing a predetermined number of X-ray images A generated successively and display the composite image D as a moving image by displaying the plurality of generated composite images D successively, but the present invention is not limited thereto.

For example, the composite image D generated by superimposing a predetermined number of successively generated X-ray images A may be displayed as a still image. Further, a single composite image D may be generated by composing all of the plurality of generated X-ray images A, and the composite image D may be displayed on the display unit 4 as a still image. In this case, the device reference shape (guidewire reference shape Gα) is acquired based on the average of the extracted feature quantities by acquiring the average coordinate of the position coordinates of the markers 203 in all X-ray images A and extracting the feature quantities from the shapes of the devices (guidewires 204) in all X-ray images A. Then, based on the acquired marker reference position Mα and guidewire reference shape Gα, all of the X-ray images A are composed.

Further, in the above-described embodiment, an example is shown in which the control unit 6 is configured by a single control unit including the device control unit 61 for controlling the device and the image controller (the detection processing unit 63 and the composition processing unit 64) for performing the image processing of the X-ray image A, but the present invention is not limited thereto. For example, the device control unit 61 and the image controller (the detection processing unit 63 and the composition processing unit 64) may be configured by separate control units. Further, by providing an image processing apparatus separately from the control unit 6, the image processing may be performed by the image processing apparatus.

Further, in the above-described embodiment, an example is shown in which one composite image D is generated by composing eight X-ray images A among the successively generated X-ray images A, when generating a moving image using a plurality of composite images D, but the present invention is not limited thereto. For example, six pieces of X-ray images A may be used to generate a single composite image D.

Further, in the above-described embodiment, an example is shown in which the X-ray imaging apparatus 100 is used for a coronary intervention treatment, but the present invention is not limited thereto. For example, it may be used for a treatment of arteriosclerosis obliterans of the lower extremity.

ASPECTS

It will be understood by those skilled in the art that the above-described exemplary embodiments are concrete examples of the following aspects.

(Item 1)

An X-ray imaging apparatus comprising:

an X-ray tube configured to irradiate a subject with X-rays;

an X-ray detector configured to detect the X-rays transmitted through the subject; and an image controller configured to generate a composite image by superimposing a plurality of X-ray images generated based on a detection signal output from the X-ray detector, wherein the image controller includes:

a detection processing unit configured to detect both a marker for indicating a position of a predetermined target object to be indwelled in a body of the subject and a device to be placed in the body of the subject separately from the predetermined target object, in the generated X-ray image; and a composition processing unit configured to generate the composite image by superimposing the plurality of X-ray images based on the marker and the device both detected by the detection processing unit.

(Item 2)

The X-ray imaging apparatus as recited in the above-described Item 1, wherein the composition processing unit is configured to generate the composite image by superimposing the plurality of X-ray images in such a manner that the markers each detected in each of the plurality of X-ray images overlap with each other and the devices each detected in each of the plurality of X-ray images overlap with each other.

(Item 3)

The X-ray imaging apparatus as recited in the above-described Item 2, wherein the detection processing unit is configured to detect a position of the marker and a shape of the device, and wherein the composition processing unit is configured to generate the composite image by superimposing the plurality of X-ray images in such a manner that the markers overlap with each other and the devices overlap with each other by deforming each of the plurality of X-ray images based on the detected position of the marker and the detected shape of the device.

(Item 4)

The X-ray imaging apparatus as recited in any one of the above-described Items 1 to 3, wherein the device is placed in the body of the subject integrally with the predetermined target object, and wherein the detection processing unit is configured to detect the marker and the device that changes in shape integrally with the predetermined target object in the body of the subject.

(Item 5)

The X-ray imaging apparatus as recited in the above-described Item 4, wherein the predetermined target object includes a stent to be indwelled in the body of the subject, wherein the device includes a guidewire used for indwelling the stent in the subject, wherein the detection processing unit is configured to detect a position of the marker for indicating a position of the stent and at least a part of a shape of the guidewire, and wherein the composition processing unit is configured to generate the composite image by superimposing the plurality of X-ray images based on a detected position of the marker and the at least a part of the shape of the detected guidewire.

(Item 6)

The X-ray imaging apparatus as recited in the above-described Item 5, wherein the marker is provided at each of both ends of the stent to indicate the position of the stent, and wherein the detection processing unit is configured to detect the position of the marker positioned at both ends of the stent and detect the shape of the guidewire positioned between the position of the marker provided at one end of the stent and the position of the marker positioned at the other end of the stent.

(Item 7)

The X-ray imaging apparatus as recited in any one of the above-described Items 1 to 6, wherein the detection processing unit is configured to detect the position of the marker and the shape of the device, and wherein the composition processing unit is configured to generate the composite image by superimposing the plurality of X-ray images in such a manner that the markers overlap at a marker reference position acquired based on the positions of the plurality of markers each detected in each of the plurality of X-ray images and the devices overlap with a device reference shape acquired based on the shapes of the plurality of devices each detected in each of the plurality of X-ray images.

(Item 8)

The X-ray imaging apparatus as recited in the above-described Item 7, wherein the marker reference position is an average position of the markers each detected in each of the plurality of X-ray images, wherein the device reference shape is an average shape of the device shapes each detected in each of the plurality of X-ray image, and wherein the composition processing unit is configured to generate the composite image by superimposing the plurality of X-ray images in such a manner that the markers each detected in each of the plurality of X-ray images overlap at the marker reference position and the devices each detected in each of the plurality of X-ray images overlap with the device reference shape.

(Item 9)

The X-ray imaging apparatus as recited in any one of the above-described Items 1 to 8, wherein the composition processing unit is configured to generate the composite image by superimposing a predetermined number of successively generated X-ray images and display the composite image as a moving image by successively displaying the plurality of generated composite images.

(Item 10)

An X-ray image processing method comprising the steps of:

generating an X-ray image by detecting X-rays that have transmitted through a subject;

detecting both a marker for indicating a position of a predetermined target object to be indwelled in a body of a subject and a device to be placed in the body of the subject separately from the predetermined target object, in the generated X-ray image; and generating a composite image by superimposing the plurality of X-ray images based on the detected marker and the detected device.

The invention claimed is:

1. An X-ray imaging apparatus comprising:
an X-ray tube configured to irradiate a subject with X-rays;
an X-ray detector configured to detect the X-rays transmitted through the subject; and
an image control processor configured to generate a composite image by superimposing a plurality of X-ray images generated based on a detection signal output from the X-ray detector,
wherein the image control processor is configured to detect, in each of the plurality of X-ray images generated based on the detection signal output from the X-ray detector, both a marker for indicating a position of a predetermined target object to be indwelled in a body of the subject and a shape of a device to be placed in the body of the subject separately from the predetermined target object, wherein the image control processor is configured to deform each of the plurality of X-ray images in such a manner that the devices in the plurality of X-ray images overlap with each other and generate the composite image by superimposing the plurality of deformed X-ray images based on the marker and the shape of the device both detected in each of the plurality of X-ray images, and wherein the image control processor is configured to generate the composite image by superimposing the plurality of deformed X-ray images in such a manner that the devices overlap with a device reference shape that is an average shape of the device shapes detected in the plurality of X-ray images.

2. The X-ray imaging apparatus as recited in claim 1, wherein the image control processor is configured to generate the composite image by superimposing the plurality of deformed X-ray images in such a manner that the markers detected in the plurality of X-ray images overlap with each other and the devices detected in the plurality of X-ray images overlap with each other.

3. The X-ray imaging apparatus as recited in claim 2, wherein the image control processor is configured to detect, in each of the plurality of X-ray images generated based on the detection signal output from the X-ray detector, a position of the marker and the shape of the device, and wherein the image control processor is configured to generate the composite image by superimposing the plurality of deformed X-ray images in such a manner that the markers overlap with each other and the devices overlap with each other by deforming each of the plurality of X-ray images based on the detected position of the marker and the detected shape of the device.

4. The X-ray imaging apparatus as recited in claim 1, wherein the device is placed in the body of the subject along with the predetermined target object, and wherein the image control processor is configured to detect the marker and the device that changes in shape integrally with the predetermined target object in the body of the subject.

5. The X-ray imaging apparatus as recited in claim 4, wherein the predetermined target object includes a stent to be indwelled in the body of the subject, wherein the device includes a guidewire used for indwelling the stent in the subject, wherein the image control processor is configured to detect, in each of the plurality of X-ray images generated based on the detection signal output from the X-ray detector, a position of the marker for indicating a position of the stent and at least a part of a shape of the guidewire, and wherein the image control processor is configured to generate the composite image by superimposing the plurality of deformed X-ray images based on a detected position of the marker and the at least the part of the shape of the detected guidewire.

6. The X-ray imaging apparatus as recited in claim 5, wherein the marker comprises a first marker and a second marker, wherein the first marker is provided at a first end of the stent and the second marker is provided at a second end of the stent to indicate the position of the stent, and wherein the image control processor is configured to detect the position of the marker positioned at both ends of the stent and detect the shape of the guidewire positioned between the position of the marker provided at one end of the stent and the position of the marker positioned at the other end of the stent.

7. The X-ray imaging apparatus as recited in claim 1, wherein the image control processor is configured to detect, in each of the plurality of X-ray images generated based on the detection signal output from the X-ray detector, a position of the marker and the shape of the device, and wherein the image control processor is configured to generate the composite image by superimposing the plurality of deformed X-ray images in such a manner that the markers overlap at a marker reference position acquired based on the position of the marker detected in each of the plurality of X-ray images and the devices overlap with the device reference shape acquired based on the shape of the device detected in each of the plurality of X-ray images.

8. The X-ray imaging apparatus as recited in claim 7, wherein the marker reference position is an average position of the markers detected in the plurality of X-ray images, and wherein the image control processor is configured to generate the composite image by superimposing the plurality of deformed X-ray images in such a manner that the markers detected in the plurality of X-ray images overlap at the marker reference position and the devices detected in the plurality of X-ray images overlap with the device reference shape.

9. The X-ray imaging apparatus as recited in claim 1, wherein the image control processor is configured to generate the composite image by superimposing a predetermined number of X-ray images that are successively generated and display the composite image as a moving image by successively displaying a plurality of generated composite images.

10. An X-ray image processing method comprising the steps of:

generating a plurality of X-ray images by detecting X-rays that have transmitted through a subject;

detecting, in each of the plurality of X-ray images, both a marker for indicating a position of a predetermined target object to be indwelled in a body of a subject and a shape of a device to be placed in the body of the subject separately from the predetermined target object;

deforming each of the plurality of X-ray images in such a manner the devices in the plurality of X-ray images overlap with each other; and generating a composite image by superimposing the plurality of deformed X-ray images based on the detected marker and the shape of the detected device in each of the plurality of X-ray images, wherein the generating the composite image includes generating the composite image by superimposing the plurality of deformed X-ray images in such a manner that the devices overlap with a device reference shape that is an average shape of the device shapes detected in the plurality of X-ray images.

* * * * *